(12) United States Patent
Pandurang et al.

(10) Patent No.: US 9,102,646 B2
(45) Date of Patent: Aug. 11, 2015

(54) PROCESS FOR THE PRODUCTION OF 4-SUBSTITUTED CHROMANES VIA GOLD CATALYSIS

(71) Applicant: Council of Scientific and Industrial Research, New Delhi (IN)

(72) Inventors: Vilasrao Chouthaiwale Pandurang, Pune (IN); Ambadas Devalankar Dattatray, Pune (IN); Arumugam Sudalai, Pune (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 14/365,527

(22) PCT Filed: Dec. 17, 2012

(86) PCT No.: PCT/IN2012/000823
§ 371 (c)(1),
(2) Date: Jun. 13, 2014

(87) PCT Pub. No.: WO2013/088455
PCT Pub. Date: Jun. 20, 2013

(65) Prior Publication Data
US 2015/0005514 A1    Jan. 1, 2015

(30) Foreign Application Priority Data
Dec. 15, 2011    (IN) .......................... 3659/DEL/2011

(51) Int. Cl.
C07D 311/04        (2006.01)
C07D 311/58        (2006.01)
C07D 493/04        (2006.01)

(52) U.S. Cl.
CPC ............ *C07D 311/04* (2013.01); *C07D 311/58* (2013.01); *C07D 493/04* (2013.01)

(58) Field of Classification Search
CPC ... C07D 311/04; C07D 311/58; C07D 493/04
See application file for complete search history.

(56) References Cited

FOREIGN PATENT DOCUMENTS

JP    2005-254034 A    9/2005
WO    WO-2013/088455 A1    6/2013

OTHER PUBLICATIONS

Collett et al. (J. C. S. Chem. Comm., 1976; p. 708-709).*
"International Application No. PCT/IN2012/000823, Demand and Response filed Oct. 7, 2013 to International Search Report mailed on Mar. 1, 2013", 10 pgs.
"International Application No. PCT/IN2012/000823, International Preliminary Report on Patentability dated May 28, 2014", 9 pgs.
"International Application No. PCT/IN2012/000823, International Search Report mailed Mar. 1, 2013", 5 pgs.
"International Application No. PCT/IN2012/000823, Written Opinion mailed Mar. 1, 2013", 6 pgs.
Hong. Liang, et al., "ChemInform® Abstract: Organocatalytic Asymmetric Friedel—Crafts Alkylation/Cyclization Cascade Reaction of 1-Naphthols and α,β-Unsaturated Aldehydes: An Enantioselective Synthesis of Chromans and Dihydrobenzopyrans", *ChemInform*, 41(4), (2010), 1 pg.
Iwai, Issei, et al., "Studies on Acetylenic Compounds. XXIII. A New Ring Closure of 2-Propynyl Ethers", *Chemical & Pharmaceutical Bulletin*, 10(10), (1962), 926-933.
Kang, Han-Young, et al., "Synthesis of Chromane Derivatives via Indium-mediated Intramolecular Allenylation and Allylation to Imines", *Bull. Korean Chem. Soc.*, 25(11), (2004), 1627-1628.
Katritzky, Alan R., et al., "Functionalized (Benzotriazol-1-yl)methanes as 1,1-Dipole Synthon Equivalents in Diverse Annulations to Aromatic and Heteroaromatic Rings", *J. Org. Chem.*, 63, (1998), 3445-3449.
Nguyen, Van Cuong, "Synthesis of Chromane Derivatives by Palladium-Catalyzed Intramolecular Allylation of Aldehydes with Allylic Acetates or Chlorides Using Indium and Indium (III) Chloride", *Bull Korean Chem. Soc.*, 26(5), (2005), 711-712.
Rossinskii, A. P., et al., "Condensation of aromatic compounds with halogen derivatives of allylic type. XIX, Thermal and catalytic rearrangement of 4-(3-phenyl-2-propenoxy)toluene", *Journal of Organic Chemistry of the USSR*, vol. 10, (1974), 2402-2406.
Xie, Kai, et al., "Synthesis of tetralin and chromane derivatives via In-catalyzed intramolecular hydroarylation", *Tetrahedron Letters*, 51(33), (2010), 4466-4469.

* cited by examiner

*Primary Examiner* — Valerie Rodriguez-Garcia
(74) *Attorney, Agent, or Firm* — Schwegman Lundberg & Woessner, P.A.

(57) ABSTRACT

Disclosed herein is single step process for the synthesis of 4-aryl substituted chromanes of compound of formula 2 comprising subjecting 3-aryloxy-1-phenylpropan-1-ol of formula 1 to (III) chloride-catalyzed intramolecular Friedel-Crafts reaction to obtain 4-aryl substituted chromanes. The invention further discloses novel 4-substituted Chromane compounds.

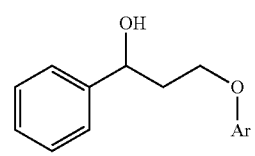

Formula 1

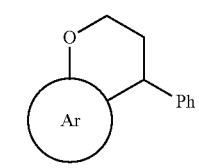

Formula 2

6 Claims, No Drawings

PROCESS FOR THE PRODUCTION OF 4-SUBSTITUTED CHROMANES VIA GOLD CATALYSIS

PRIORITY CLAIM TO RELATED APPLICATIONS

This application is a U.S. national stage application filed under 35 U.S.C. §371 from International Application Serial No. PCT/IN2012/000823, which was filed Dec. 17, 2012, and published as WO 2013/088455 on Jun. 20, 2013, and which claims priority to Indian Application No. 3659/DEL/2011, filed Dec. 15, 2011, which applications and publication are incorporated by reference as if reproduced herein and made a part hereof in their entirety, and the benefit of priority of each of which is claimed herein.

TECHNICAL FIELD OF THE INVENTION

Present invention relates to synthesis of 4-aryl substituted chromanes by using gold (III) chloride-catalyzed intramolecular Friedel-Crafts reaction of 3-aryloxy benzyl alcohol. The invention further relates to novel 4-substituted Chromane.

BACKGROUND AND PRIOR ART OF THE INVENTION

The structure of chromanes is abundant in natural products that possess a broad array of biological activities such as antimicrobial, antiviral, anti-proliferative and antitumor activity. Since chromanes are found in many natural products, efficient construction of this ring structure has attracted much attention in the recent past.

Synthesis of Chromane Derivatives via Indium-mediated Intramolecular Allenylation and Allylation to Imines as in scheme 1 is disclosed by Han-Young Kang et al. in Bull. Korean Chem. Soc. 2004, Vol. 25, No. 11, 1627-1628. However, the reported yields are poor in the range of 70-80%.

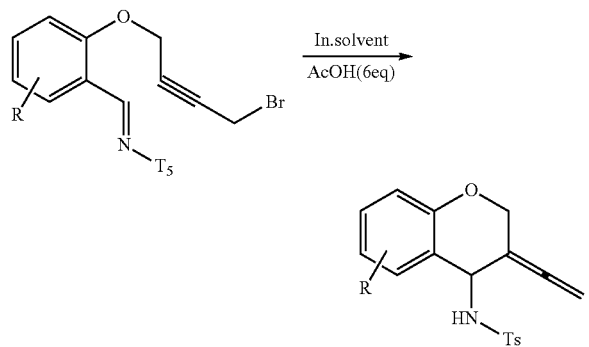

Scheme 1

Synthesis of Chromane Derivatives by Palladium-Catalyzed Intramolecular Allylation of Aldehydes with Allylic Acetates or Chlorides using Indium and Indium(III) Chloride as in scheme 2 is reported by Van Cuong Nguyen et al. in Bull. Korean Chem. Soc. 2005, Vol. 26, No. 5, page 711-712. However, the yields reported are poor in the range of 40-80%.

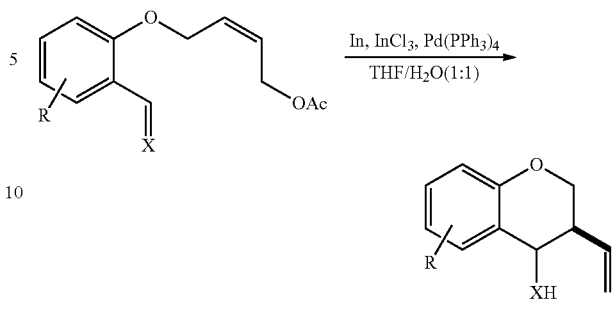

Scheme 2

Synthesis of tetralin and chromane derivatives via In-catalyzed intramolecul arhydroarylationas in scheme 3 is reported by Kai Xie et al., in Tetrahedron Letters Volume 51, Issue 33, 18 Aug. 2010, Pages 4466-4469. According to this study, $In(OTf)_3$ was found to be an effective catalyst for the cyclization of ω-aryl-1-alkenes to form tetralin and chromane derivatives.

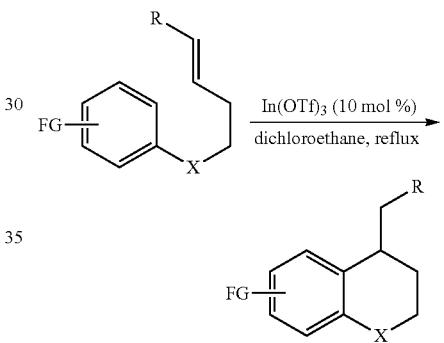

Scheme 3

X = C, NR, O

Though the use of indium provides cost advantage over the use of palladium/platinum catalysts, the cursory review of prior art methods shows that the yields of the chromane obtained are not exceeded 80% and again the purification of the desired product and recycling of unreacted reagents adds additional steps to the synthesis.

Most of the reported methods for synthesis of chromanes are run under harsh conditions with high concentration of Lewis acids, which can hardly be tolerated by many functional groups.

In the light of the above, the present inventors have aimed at the alternate provision of efficient method for the synthesis of important chroman structure that possess a broad array of biological activities such as antimicrobial, antiviral, antiproliferative and antitumor activity.

OBJECTIVE OF THE INVENTION

Main object of the present invention is to provide synthesis of 4-aryl substituted chromanes by using gold (III) chloride-catalyzed intramolecular Friedel-Crafts reaction of 3-aryloxy benzyl alcohol.

Another objective of the present invention is to provide novel 4-substituted Chromanes.

Yet another objective of the [present invention is to provide an efficient method to synthesize the compounds having this important active moiety in good yields by single catalytic method.

SUMMARY OF THE INVENTION

Accordingly, present invention provides a single step process for the synthesis of 4-aryl substituted chromanes of compound of formula 2

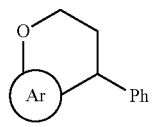

Formula 2 comprising subjecting 3-aryloxy-1-phenylpropan-1-ol of formula 1 to gold (III) chloride-catalyzed intramolecular Friedel-Crafts reaction to obtain 4-aryl substituted chromanes

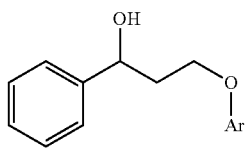

Formula 1 wherein 'Ar' is selected from the group consisting of α-Naphthyl, 4-Methylphenyl, Phenyl, β-Naphthyl, 4-Chlorophenyl, 4-Bromophenyl, 4-Fluorophenyl, 4-Cyanophenyl, Cesamoyl, 2-Methylphenyl, 2-Chlorophenyl, 2-Brormophenyl.

In an embodiment of the present invention, the process is carried out at temperature in the range of 20 to 30° C.

In yet another embodiment of the present invention, the process is carried out in presence of a solvent selected from the group consisting of halogenated hydrocarbons.

In yet another embodiment of the present invention, the molar ratios of the 3-aryloxy-1-phenylpropan-1-ol with reference to gold(III) chloride is in the range of 1:0.01.

In yet another embodiment of the present invention, the formula 2 is selected from the group consisting of:

a) 3,4-Dihydro-4-phenyl-2H-benzo[h]chromene
b) 3,4-Dihydro-(6-methyl-4-phenyl)-2H-chromene
c) 3,4-Dihydro-4-phenyl-2H-chromene
d) 2,3-dihydro-1-phenyl-1H-benzo[f]chromene
e) 6-Chloro-3,4-dihydro-4-phenyl-2H-chromene
f) 3,4-Dihydro-4-phenyl-2H-chromene-6-carbonitrile
g) 7,8-Dihydro-8-phenyl-6H-1,3-dioxalo-4,5-chromene
h) 6-methoxy-3,4-dihydro-4-phenyl-2H-chromene
i) 6-bromo-3,4-dihydro-4-phenyl-2H-chromene and
j) 6-trifluoromethyl)-3,4-dihydro-4-phenyl-2H-chromene.

In yet another embodiment, present invention provides compound of formula 2

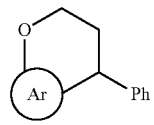

Formula 2 wherein 'A' is selected from the group consisting of α-Naphthyl, 4-Methylphenyl, Phenyl, β-Naphthyl, 4-Chlorophenyl, 4-Bromophenyl, 4-Fluorophenyl, 4-Cyanophenyl, Cesamoyl, 2-Methylphenyl, 2-Bromophenyl, 2-Chlorophenyl.

In yet another embodiment of the present invention, The compounds of formula 2 comprises:

a) 3,4-Dihydro-4-phenyl-2H-benzo[h]chromene
b) 3,4-Dihydro-(6-methyl-4-phenyl)-2H-chromene
c) 3,4-Dihydro-4-phenyl-2H-chromene
d) 2,3-dihydro-1-phenyl-1H-benzo[f]chromene
e) 6-Chloro-3,4-dihydro-4-phenyl-2H-chromene
f) 3,4-Dihydro-4-phenyl-2H-chromene-6-carbonitrile
g) 7,8-Dihydro-8-phenyl-6H-1,3-dioxalo-4,5-chromene

DETAILED DESCRIPTION OF THE INVENTION

Present invention provides catalytic single step process for the synthesis of 4-aryl substituted chromanes of compound of formula 2 using gold (III) chloride-catalyzed intra-molecular Friedel-Crafts reaction of 3-aryloxy-1-phenylpropan-1-ol of formula 1.

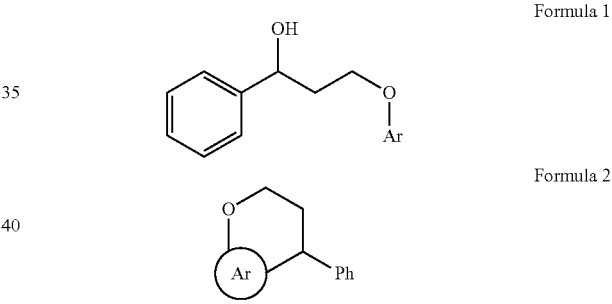

wherein Ar as shown in formula 1 and 2 is selected from the group consisting of α-Naphthyl, 4-Methylphenyl, Phenyl, β-Naphthyl, 4-Chlorophenyl, 4-Bromophenyl, 4-Fluorophenyl, 4-Cyanophenyl, Cesamoyl, 2-Methylphenyl, 2-Chlorophenyl, 2-Brormophenyl. what is this cesamoyl group kindly add structure here etc.

The advantage of the instant invention is being a single step catalytic process that can be conducted under milder reaction conditions with high yields. The gold (III) chloride-catalyzed intramolecular Friedel-Crafts reaction of 3-aryloxy-1-phenylpropan-1-ol of formula 1 may effectively be carried out at room temperature i.e. at 20 to 30° C.

The process is carried out in presence of a solvent selected from the group consisting of halogenated hydrocarbons.

3-aryloxy-1-phenylpropan-1-ol of formula 1 is subjected to gold(III) chloride-catalyzed Friedel-Crafts intramolecular cyclization in dichloromethane as a solvent at room temperature, to yield 4-aryl substituted chromanes of formula 2 in good yields. The molar ratios of the 3-aryloxy-1-phenylpropan-1-ol with reference to gold(III) chloride is in the range of 1:0.01 and the reaction may be accomplished in about 4-8 hrs.

As mentioned herein the phrase 'room temperature' means and includes a temperature range of 20 to 30° C.

Similarly, the instant invention provides process for preparation of a library of compounds of formula 2 using gold (III) chloride-catalyzed intramolecular Friedel-Crafts reaction of 3-aryloxy-1-phenylpropan-1-ol of formula 1. The formula 2 of the instant invention prepared according to the process of the invention encompasses the following compounds:

a) 3,4-Dihydro-4-phenyl-2H-benzo chromene

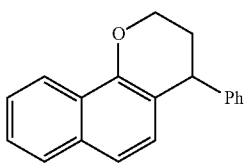 [SMILES: c1ccc(C2CCOc3c2ccc2ccccc32)cc1]

b) 3,4-Dihydro-(6-methyl-4-phenyl)-2H-chromene

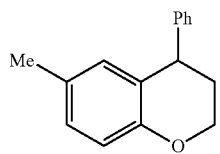

c) 3,4-Dihydro-4-phenyl-2H-chromene

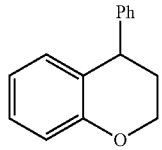 [SMILES: c1ccc(C2CCOc3ccccc32)cc1]

d) 2,3-dihydro-1-phenyl-1H-benzo[f]chromene

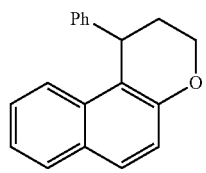 [SMILES: c1ccc(C2CCOc3ccc4ccccc4c32)cc1]

e) 6-Chloro-3,4-dihydro-4-phenyl-2H-chromene

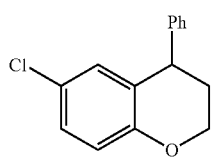

f) 3,4-Dihydro-4-phenyl-2H-chromene-6-carbonitrile

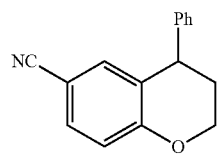 [SMILES: N#Cc1ccc2c(c1)C(c1ccccc1)CCO2]

g) 7,8-Dihydro-8-phenyl-6H-1,3-dioxalo-4,5-chromene

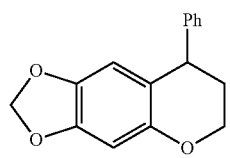 [SMILES: c1ccc(C2CCOc3cc4c(cc32)OCO4)cc1]

The invention provides novel compounds of formula 2

Formula 2

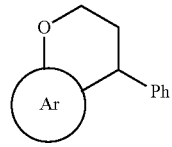

wherein 'Ar' is selected from the group consisting of α-Naphthyl, Methylphenyl, ethylphenyl, Phenyl, β-Naphthyl, Chlorophenyl, bromophenyl, iodo phenyl, fluorophenyl, Cyanophenyl, methoxyphenyl, trifluoromethylphenyl and Cesamoyl.

EXAMPLES

Following examples are given by way of illustration and therefore should not be construed to limit the scope of the invention.

Example 1

To a solution of gold(III) chloride (3 mg, 1 mol %), in $CH_2Cl_2$ (5 mL) was added 3-(naphthalen-1-yloxy)-1-phenylpropan-1-ol 1a (278 mg, 1 mmol) in (2 mL $CH_2Cl_2$) at 25° C. The resulting mixture was stirred for 6 h at 25° C. After stirring 6 h reaction mixture was quenched with water and extracted with $CH_2Cl_2$ (10 mL×2). The organic layer was washed with brine and dried over anhydrous $Na_2SO_4$. The solvent was concentrated in vacuo and the residue was purified by column chromatography (pet. Ether:ethyl acetate=9:1) to afford the desired cyclized product 3,4-dihydro-4-phenyl-2H-benzo[h]chromene or 4-aryl substituted chromanes (2a) in 98% yields.

Example 2

To study the generality of the reaction, several 3-aryloxy-1-phenylpropan-1-ol (1a-g) were subjected to $AuCl_3$-catalyzed Friedel-Crafts intramolecular cyclization the results of which are presented in Table 1. It is observed that 3-phenoxy-1-phenylpropan-1-ol as well as 3-(naphthalen-1-yloxy)-1-phenylpropan-1-ol gave good yields. In the case of both electron-donating (1b) as well as electron-withdrawing (1f) substituted 3-aryloxy-1-phenylpropan-1-ol gave the corresponding chromanes in 98% and 90% yields respectively.

TABLE 1

Synthesis of 4-aryl substituted chromanes[a]

| Entry | Substrate (1a-g) | Product (2a-g) | Yield (%)[b] |
|---|---|---|---|
| a | | | 98 |
| b | | | 98 |
| c | | | 96 |
| d | | | 97 |
| e | | | 93 |
| f | | | 90 |
| g | | | 93 |

Reaction conditions:
[a] 3-aryloxy benzyl alcohols (1 mmol), AuCl$_3$ (1 mol %), CH$_2$Cl$_2$ (5 mL) 25° C., 4-8 h;
[b] yields refer to isolated yields after column chromatography.

3,4-Dihydro-4-phenyl-2H-benzo[h]chromene (2a)

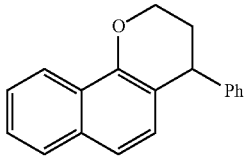 [SMILES: c1ccc(C2CCOc3c2ccc2ccccc32)cc1]

Yield: 98%; colorless solid m.p.: 82° C.; IR (CHCl$_3$, cm$^{-1}$): 701, 768, 1023, 1105, 1216, 1262, 1403, 1404, 1491, 1507, 1576, 2882, 2954, 3019, 3057; $^1$H NMR (200 MHz, CDCl$_3$): δ 2.07-2.22 (m, 1H), 2.37-2.53 (m, 1H), 4.26-4.38 (m, 3H), 6.92 (d J=8.1 Hz, 1H), 7.11-7.32 (m, 6H), 7.40-7.50 (m, 2H), 7.68-7.74 (m, 1H), 8.18-8.22 (m, 1H); $^{13}$C NMR (50 MHz, CDCl$_3$): 31.8, 40.9, 63.6, 117.4, 119.7, 121.8, 125.2, 126.0, 126.4, 127.4, 128.2, 128.4, 128.7, 133.5, 145.9, 150.3; Anal. Calcd for C$_{19}$H$_{16}$O requires C, 87.66; H, 6.19. found: C, 87.60; H, 6.25%.

3,4-Dihydro-(6-methyl-4-phenyl)-2H-chromene (2b)

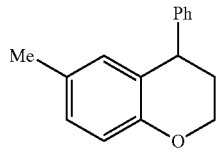

Yield: 98%; colorless gum; IR (CHCl$_3$, cm$^{-1}$): 768, 1023, 1107, 1218, 1266, 1403, 1404, 1491, 1508, 1576, 2884, 2954, 3019, 3050; $^1$H NMR (200 MHz, CDCl$_3$): δ 1.97-2.12 (m, 1H), 2.16 (s, 3H), 2.22-2.37 (m, 1H), 4.08-4.16 (m, 3H), 6.61-6.62 (m, 1H), 6.74 (d, J=8.3 Hz, 1H), 6.89-6.94 (m, 1H), 7.10-7.33 (m, 5H); $^{13}$C NMR (50 MHz, CDCl$_3$): 20.5, 31.8, 41.0, 63.4, 116.5, 123.8, 126.4, 128.4, 128.5, 128.6, 129.2, 130.7, 145.8, 153.0; Anal. Calcd for C$_{16}$H$_{16}$O requires C, 85.68; H, 7.19. found: C, 85.70; H, 7.25%.

3,4-Dihydro-4-phenyl-2H-chromene (2c)

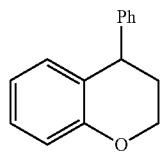 [SMILES: c1ccc(C2CCOc3ccccc32)cc1]

Yield: 96%; gum; IR (CHCl$_3$, cm$^{-1}$): 768, 1030, 1107, 1220, 1266, 1406, 1404, 1491, 1508, 1576, 2882, 2950, 3019, 3051; $^1$H NMR (200 MHz, CDCl$_3$): δ 2.04-2.14 (m, 1H), 2.27-2.36 (m, 1H), 4.13-4.20 (m, 3H), 6.73-6.86 (m, 3H), 7.07-7.33 (m, 6H); $^{13}$C NMR (50 MHz, CDCl$_3$): 20.5, 31.8, 41.0, 63.4, 116.5, 123.8, 126.4, 128.4, 128.5, 128.6, 129.2, 130.7, 145.8, 153.0; Anal. Calcd for C$_{15}$H$_{14}$O requires C, 85.68; H, 6.71. found: C, 85.72; H, 6.67%.

2,3-dihydro-1-phenyl-1H-benzo[f]chromene (2d)

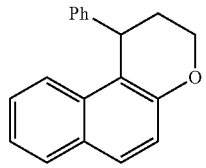 [SMILES: c1ccc(C2CCOc3ccc4ccccc4c32)cc1]

Yield: 97%; colorless solid m.p.: 85° C.; IR (CHCl$_3$, cm$^{-1}$): 701, 768, 1023, 1105, 1216, 1262, 1403, 1404, 1491, 1507, 1576, 2882, 2954, 3019, 3057; $^1$H NMR (200 MHz, CDCl$_3$): δ 2.10 (qd, J=2.2, 6.9 Hz, 1H), 2.43-2.61 (m, 1H), 4.07 (td, J=2.0, 10.4 Hz, 1H), 4.19-4.28 (m, 1H), 5.11 (d, J=5.2 Hz, 1H), 7.08-7.28 (m, 8H), 7.44-7.99 (m, 1H), 7.66-7.74 (m, 2H); $^{13}$C NMR (50 MHz, CDCl$_3$): 30.9, 36.8, 61.3, 114.1, 119.0, 123.0, 123.1, 126.3, 126.4, 128.4, 128.5, 128.8, 129.2, 133.0, 145.8, 153.0; Anal. Calcd for C$_{19}$H$_{16}$O requires C, 87.66; H, 6.19. found: C, 87.60; H, 6.25%.

6-Chloro-3,4-dihydro-4-phenyl-2H-chromene (2e)

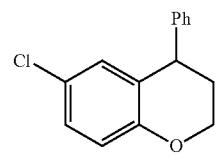 [SMILES: Clc1ccc2c(c1)C(c1ccccc1)CCO2]

Yield: 93%; pale yellow gum; IR (CHCl$_3$, cm$^{-1}$): 766, 1030, 1100, 1218, 1260, 1403, 1404, 1491, 1508, 1576, 2884, 2952, 3010, 3045; $^1$H NMR (200 MHz, CDCl$_3$): δ 1.99-2.14 (m, 1H), 2.21-2.36 (m, 1H), 4.09-4.19 (m, 3H), 6.76-6.82 (m, 1H), 7.03-7.13 (m, 3H), 7.16-7.36 (m, 4H); $^{13}$C NMR (50 MHz, CDCl$_3$): 31.3, 41.0, 63.8, 118.2, 125.1, 126.0, 127.9, 128.5, 128.6, 130.0, 144.8, 153.7; Anal. Calcd for C$_{15}$H$_{13}$ClO requires C, 73.62; H, 5.35. found: C, 73.60; H, 5.40%.

3,4-Dihydro-4-phenyl-2H-chromene-6-carbonitrile (2f)

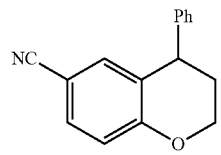 [SMILES: N#Cc1ccc2c(c1)C(c1ccccc1)CCO2]

Yield: 90%; colorless gum; IR (CHCl$_3$, cm$^{-1}$): 768, 1023, 1103, 1218, 1266, 1403, 1410, 1491, 1510, 1576, 2210, 2253, 2884, 2954, 3019, 3054; $^1$H NMR (200 MHz, CDCl$_3$): δ 2.01-2.14 (m, 1H), 2.21-2.39 (m, 1H), 4.06-4.18 (m, 1H), 4.26 (t, J=5.1 Hz, 2H), 6.90 (d, J=8.3 Hz, 1H), 7.05-7.15 (m, 3H), 7.26-7.43 (m, 4H); Anal. Calcd for C$_{16}$H$_{13}$NO requires C, 81.68; H, 5.57; N, 5.95. found: C, 81.60; H, 5.60; N, 5.91%.

7,8-Dihydro-8-phenyl-6H-1,3-dioxalo-4,5-chromene (2g)

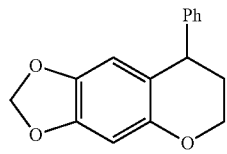 [SMILES: c1ccc(C2CCOc3cc4c(cc32)OCO4)cc1]

Yield: 93%; colorless gum; IR (CHCl$_3$, cm$^{-1}$): 765, 1023, 1107, 1218, 1266, 1403, 1409, 1491, 15108, 1576, 2884, 2954, 3019, 3057; $^1$H NMR (200 MHz, CDCl$_3$): δ 1.99-2.09 (m, 1H), 2.23-2.35 (m, 1H), 4.03-4.13 (m, 3H), 5.91 (s, 2H), 6.24 (s, 1H), 6.38 (s, 1H), 7.11-7.33 (m, 5H); $^{13}$C NMR (50 MHz, CDCl$_3$): 38.4, 66.1, 71.7, 98.1, 101.0, 105.7, 108.0, 125.8, 127.6, 128.5, 141.7, 144.3, 148.2, 154.2; Anal. Calcd for C$_{16}$H$_{14}$O$_3$ requires C, 75.57; H, 5.55. found: C, 75.50; H, 5.65%.

ADVANTAGES OF THE INVENTION

1. Efficient single step process
2. Harsh conditions and high concentrations of Lewis acid avoided.

We claim:

1. A single step process for the synthesis of 4-aryl substituted chromanes of Formula 2

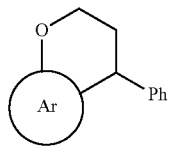

Formula 2 comprising subjecting 3-aryloxy-1-phenylpropan-1-ol of Formula 1 to gold (III) chloride-catalyzed intramolecular Friedel-Crafts reaction to obtain 4-aryl substituted chromanes of Formula 2

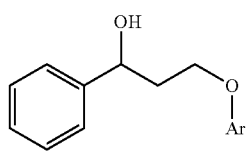

Formula 1 wherein 'Ar' is selected from the group consisting of α-Naphthyl, 4-Methylphenyl, Phenyl, β-Naphthyl, 4-Chlorophenyl, 4-Bromophenyl, 4-Fluorophenyl, 4-Cyanophenyl, 2-Methylphenyl, 2-Chlorophenyl and 2-Bromophenyl.

2. The process according to claim 1, wherein, the process is carried out at temperature in the range of 20 to 30° C.

3. The process according to claim 1, wherein the process is carried out in presence of a solvent selected from the group consisting of halogenated hydrocarbons.

4. The process according to claim 1, wherein the molar ratio of the 3-aryloxy-1-phenylpropan-1-ol with reference to gold(III)chloride is 1:0.01.

5. The process according to claim 1, wherein the compound of Formula 2 is selected from the group consisting of:
   a) 3,4-Dihydro-4-phenyl-2H-benzo[h]chromene
   b) 3,4-Dihydro-(6-methyl-4-phenyl)-2H-chromene
   c) 3,4-Dihydro-4-phenyl-2H-chromene
   d) 2,3-dihydro-1-phenyl-1H-benzo[f]chromene
   e) 6-Chloro-3,4-dihydro-4-phenyl-2H-chromene
   f) 3,4-Dihydro-4-phenyl-2H-chromene-6-carbonitrile
   h) 6-methoxy-3,4-dihydro-4-phenyl-2H-chromene
   i) 6-bromo-3,4-dihydro-4-phenyl-2H-chromene and
   j) 6-trifluoromethyl)-3,4-dihydro-4-phenyl-2H-chromene.

6. A single step process for the synthesis of 4-aryl substituted chromane of formula:

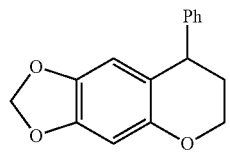 [SMILES: c1ccc(C2CCOc3cc4c(cc32)OCO4)cc1]

comprising subjecting a 3-aryloxy-1-phenylpropan-1-ol of formula:

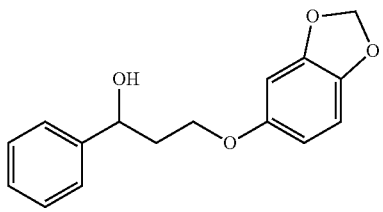 [SMILES: OC(CCOc1ccc2c(c1)OCO2)c1ccccc1]

to gold (III) chloride-catalyzed intramolecular Friedel-Crafts reaction to obtain a 4-aryl substituted chromane of formula:

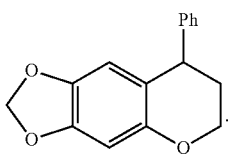 [SMILES: c1ccc(C2CCOc3cc4c(cc32)OCO4)cc1]

* * * * *